United States Patent
Bhardwaj et al.

(10) Patent No.: US 6,929,784 B1
(45) Date of Patent: Aug. 16, 2005

(54) CHLOROTRIFUORINE GAS GENERATOR SYSTEM

(75) Inventors: Jyoti Kiron Bhardwaj, Bristol (GB); Nicholas Shepherd, Cardiff (GB); Leslie Michael Lea, Oxfordshire (GB); Graham Hodgson, Lancashire (GB)

(73) Assignee: Surface Technology Systems plc, Newport (GB)

( * ) Notice: Subject to any disclaimer, the term of this patent is extended or adjusted under 35 U.S.C. 154(b) by 0 days.

(21) Appl. No.: 09/674,660

(22) PCT Filed: Mar. 6, 2000

(86) PCT No.: PCT/GB00/00796

§ 371 (c)(1),
(2), (4) Date: Nov. 3, 2000

(87) PCT Pub. No.: WO00/51938

PCT Pub. Date: Sep. 8, 2000

(30) Foreign Application Priority Data

Mar. 4, 1999 (GB) .................................... 9904925
Apr. 29, 1999 (GB) .................................... 9909856

(51) Int. Cl.[7] .............................. B01J 8/04; A61L 9/00
(52) U.S. Cl. ...................... 422/188; 422/193; 422/307; 422/305; 422/306; 422/906; 423/464; 423/466; 156/354.29; 156/354.33; 427/248.1; 427/255.39; 427/255.7; 427/533; 427/534; 427/535; 427/307

(58) Field of Search ................................ 423/464, 466; 156/354.29, 354.33; 422/307, 188, 193, 305, 422/306, 906; 427/248.1, 255.39, 255.7, 427/533

(56) References Cited

U.S. PATENT DOCUMENTS 3,876,754 A * 4/1975 Pursley ........................ 423/466
5,688,384 A * 11/1997 Hodgson et al. .......... 204/228.2
6,841,141 B2 * 1/2005 Arno et al. .................. 423/490

OTHER PUBLICATIONS

Saitiq et al; Plasmaless Cleaning Process of Silicone Surface Using Chlorine Trifluoride; Mar. 19, 1990; Applied Physics Letters 56 (12); pp. 1190-1121.*

Ibbotson et al; Plasmaless Dry Etching of Silicon with Fluorine Containing Compounds; Nov. 15, 1984; Applied Physics Letters 56(10); pp. 2939-2942.*

* cited by examiner

Primary Examiner—Jerry D Johnson
Assistant Examiner—Alexis Wachtel
(74) Attorney, Agent, or Firm—Volentine Francos & Whitt, PLLC

(57) ABSTRACT

A $ClF_3$ gas generation system is provided with supply sources of chlorine (3) (for example a cylinder of compressed chlorine) and fluorine (4) (for example a fluorine generator) connected into a gas reaction chamber (2) enabling generation of $ClF_3$ gas. The reaction chamber has a valved outlet (C) for the supply of the $ClF_3$ gas to a process chamber for immediate local use.

5 Claims, 3 Drawing Sheets

CHLOROTRIFUORINE GAS GENERATOR SYSTEM

Chlorotrifluorine ($ClF_3$) is known to be a likely candidate to achieve an improved etch process capability and has recently become increasingly utilised as a "dry chamber-clean" gas to remove very effectively deposits and build-up after other plasma processes. This is more effective and used in preference to gases such as $NF_3$ which are also highly toxic, but require plasma or other excitation means to allow etching at acceptable rates.

The prior art comprises two alternative methods of $ClF_3$ supply, either using a conventional cylinder containing the precursor gas or by local electrolytic cell generation. Cylinder $ClF_3$ gas delivery systems are most commonly used and have been discussed in detail by Verma et al (Semiconductor International, July 1997, p253). Issues such as compatibility of installation materials and thermal gradients require particular attention. These design considerations can have a significant impact on the overall performance of the process.

Supply of $ClF_3$ has been available in liquid cylinder form and, very recently, developments have focused on the availability of "dry" cartridge delivery systems. This allows the delivery of $ClF_3$ (in a nitrogen carrier gas), with the advantages that there are neither liquid filled cylinders of extremely hazardous $ClF_3$ to be transported nor any special storage requirements on-site, as the dry cartridge is solid at ambient temperatures. A limitation of either the liquid cylinder or dry cartridge $ClF_3$ delivery system is that they are both subject to fluctuations in the ambient conditions, which could affect the process reproducibility. $ClF_3$ (which is a liquid at ambient temperature) is delivered from a conventional cylinder as a low vapour-pressure gas. To achieve the high gas flow rates and pressures required for processing, a single cylinder using an external-heating jacket is commonly used. This poses additional facilitation and safety requirements in order to prevent gas condensation in the delivery lines and components. The situation may be further aggravated depending upon application. For example if the gas is used in applications where it may be switched with another process gas, then the changes in the flow demands of the process may cause the gas to liquefy in the gas lines. This is because of the variable pressure, temperature and flow parameters experienced by the gas delivery system during this process.

Newer delivery systems based on electrolytic cell generation overcome some of these limitations. Such systems are only just becoming commercially available. An example is a fluorine gas generator cell as described in U.S. Pat. No. 5,688,384. However a dedicated $ClF_3$ delivery installation is still needed. Limitations of this dry cartridge $ClF_3$ delivery system include gas flow fluctuations caused by changes in the ambient conditions which will, in turn, affect the process reproducibility. The cost of the process gas is similar to that for supply of $ClF_3$ in liquid form but the dry cartridges require exchanging and this will require a service infrastructure and support to be established. In addition, this method only allows $ClF_3$ to be generated in the presence of an $N_2$ carrier gas.

$ClF_3$ suffers from a combination of increased cost over existing chemistries, greater health and safety risks and limited commercial availability. These factors combine to make the economics and practicalities of implementing this chemistry potentially difficult and/or the installation and transportation thereof extremely hazardous.

According to the invention there is provided a $ClF_3$ gas generation system wherein supply sources of chlorine and fluorine are connected into a gas reaction chamber enabling generation of $ClF_3$ gas, and the reaction chamber has a valved outlet for the supply of the $ClF_3$ gas.

The invention further extends to such a gas generator system wherein the valved outlet from the reaction chamber is connected to a single or multiple process chamber or processing tool or multiple tools in which the $ClF_3$ gas will be utilised. A tool may have more than one chamber. This invention provides for the generation of $ClF_3$ process gas on demand. The $ClF_3$ is generated locally to the process tool through the direct combination of the precursor gases, fluorine and chlorine, under controlled temperature and pressure reaction conditions. The use of the individual precursor gases offers a considerable improvement over many of the economic, and handling constraints of current methods of supplying $ClF_3$. In particular, the recent commercial availability of an appropriately scaled local high-purity fluorine generator overcomes many of the safety issues of handling pure high-purity fluorine required for the reaction.

"Locally" (or point of use) means that the delivery system is located near to a process chamber or a number of chambers or number of systems near to one another, so that the gases created can be delivered directly to the chamber or system for immediate use rather than being created off-site and transported in a suitable container for subsequent introduction into the apparatus.

Direct reaction of $Cl_2$ and $F_2$ allows the local generation of the $ClF_3$ although the specific reaction products resulting from the reaction may include other reaction by-products species in the form of $Cl_xF_y$, (and very small quantities of $Cl_2$ and $F_2$) but the dominant species can be maintained as $ClF_3$. Apart from the reaction by-product species, the generated gas can be formed to the same high purity levels as the precursor gases. This high purity is easier to maintain in a smaller scale reaction chamber compared to much larger commercial volume generation systems. For the majority of applications envisaged, the reaction by-product species defined above are not expected to represent any detrimental process issues over $ClF_3$ alone. Other benefits of this invention include lower production cost and ownership costs as well as reduced hazard to personnel.

The reaction chamber can be formed from high purity materials (such as those sold under the Trade Marks Monel (nickel/copper/iron alloy), Inconel (nickel/chromium/iron alloy) and Hastalloy (nickel/molybdenum/chromium/mangane/iron alloy)) which would not be financially feasible with large scale generation systems.

The gas generator for the invention operates with known precursor gases at or near atmospheric pressure, thus virtually eliminating the need for specialised gas delivery systems. Ideally though the gas generation system will be provided with a control system to control the rate of supply of gases from the two supply sources and through the valved outlet from the reaction chamber.

The reaction chamber may be operated at or near atmospheric pressure, going up the range from several Torr to 760 Torr. The reaction chamber temperature can be controlled at between ambient room temperature up to 600° C. generally, but probably will lie within the range of 100–400° C. Differing temperatures may be maintained in at least 2 separate zones of the reaction chamber.

The most hazardous gas used in the installation will be $Cl_2$, which is already commonly used in most fabrication plants in the utilisation of semiconductor manufacturing techniques. Other than this, there are no extremely hazardous gases in the installation, until the process demands gas generation (of fluorine gas, followed by ClF$_3$). This reduces hazardous chemical storage problems and risk of corrosion etc. Long gas lines for the local generation of fluorine on demand from a central store on the installation to the processing environment are eliminated along with the associated risks. Specialised gas delivery systems, containing hazardous chemicals, to the process equipment are also eliminated, which reduces the level of safety precautions needed to protect the operator during use and during any maintenance operations. The generation of the process gas from the ClF$_3$ gas generator is very competitive as compared with the cost requirement using high-pressure cylinders for the actual gas supply. There would be a significant reduction in the installation cost due to the reduced amount of pipe work for the additional gases and the associated safety requirements such as gas monitoring systems.

A chlorine supply source may comprise a cylinder of compressed chlorine or a chlorine generator. A fluorine supply source may be a fluorine generator.

The direct combination of precursor gases can provide ClF$_3$ for the process chamber by passing the relatively safe precursor gases through a simple heated and pressure-controlled reaction chamber that is local to the tool. The design of the system will be such as to avoid possible adverse reactions during the combination of the precursor gases that may prejudice the overall process. The ClF$_3$ reaction chamber design allows operation at pressures independent of the process chamber pressure. This can be achieved by allowing the gas product to flow into the process chamber via a pressure control system. The process chamber is then independent of the higher pressure in the reaction chamber and the delivery pressure of the supplied fluorine and chlorine.

The introduction of high purity gases removes the need to "polish" the generated ClF$_3$ to remove unwanted impurities before passing into the process chamber. The generation of fluorine locally to the tool overcomes the commercial difficulties in obtaining high purity 100% fluorine in a high pressure cylinder and in the quantities required. The choice of supply of chlorine is from high-pressure cylinders, which are commercially readily available and commonly installed within the industry. Other appropriate methods of chlorine simply may be used. Mass flow controllers may be used to precisely meter the flow of Cl$_2$ and F$_2$ into the reaction chamber.

The safety requirements for the precursor gases are already commonplace for the targeted industry. This is not the case for chlorotrifluorine. The production of chlorotrifluorine within a sub-component of a process tool eliminates additional safety precautions that would need to be taken for the supply of such gas from a centralised store. The maintenance of the complete system is eased by the absence of any ClF$_3$ when the system is not being used for processing.

The quantity of the generated gases can be regulated to that required for the specific application so that the gas consumption is optimised and excess generated gas avoided. The design of a custom-built fluorine-on-demand generator ensures that the ClF$_3$ is only produced as required from the reaction chamber. The flow rates that can be achieved are not subject to gas delivery restrictions which might be prescribed for ClF$_3$ delivery from a central store.

The invention may be performed in various ways and preferred embodiments thereof will now be described, by way of example, with reference to the accompanying drawing, in which:—

Figure 1:
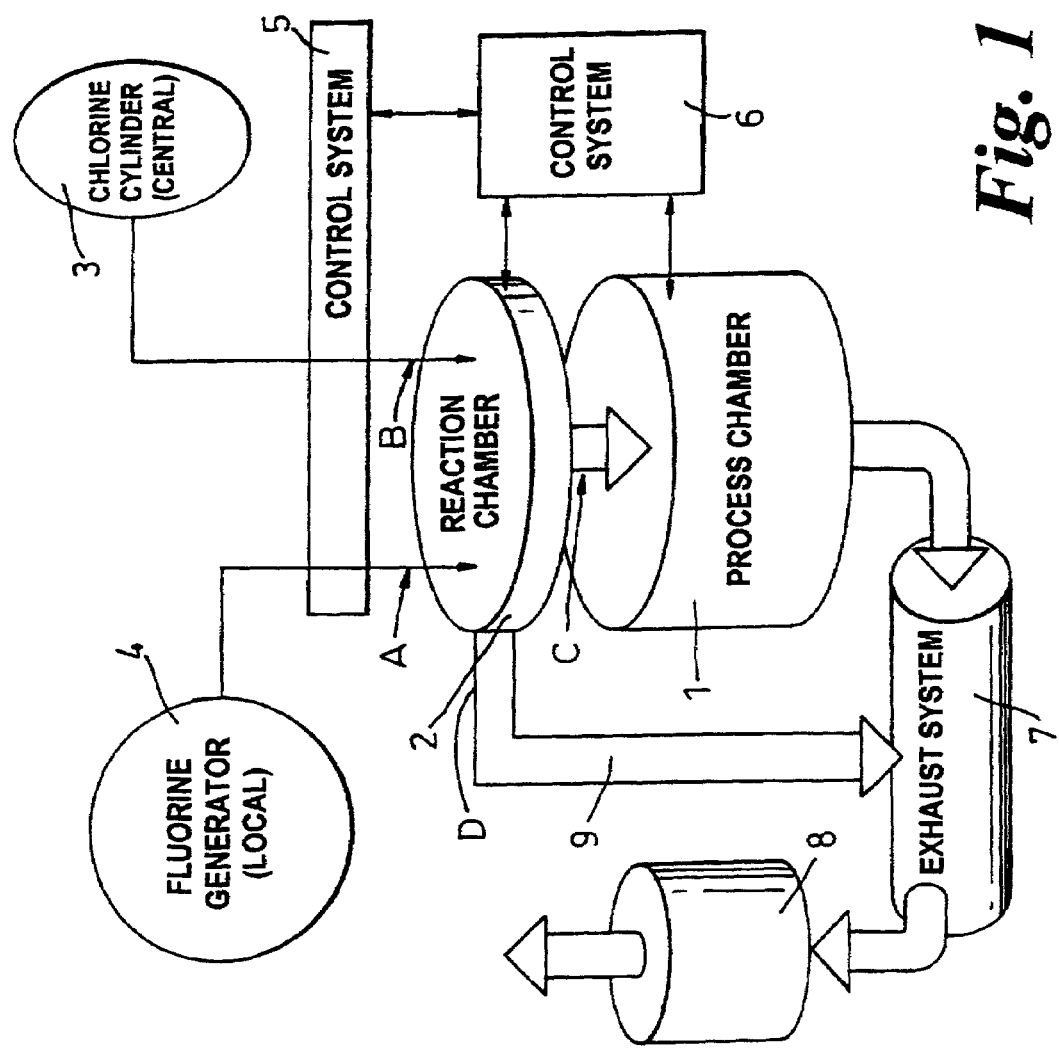
FIG. 1 is a diagrammatic illustration of a typical system of the invention.

The system shown in the drawing is for supplying chlorotrifluorine to a process chamber 1 where a dry process utilising that gas is to take place. The Cl$_3$ is delivered from a local reaction chamber 2 where precursor gases chlorine and fluorine are combined under conventional heat and pressure controlled conditions. The chlorine source is a cylinder 3 of compressed chlorine. The fluorine source is a conventional fluorine generator 4. Appropriate valving will include valves provided at A, B, C and D for appropriate isolation and control means. Linked control systems 5 and 6 monitor and maintain the supply to and conditions in the chambers 1 and 2.

From the process chamber gases pass to an exhaust system 7, which in turn leads to an abatement tool 8 (which is usually needed). A bypass outlet 9 leads from the reaction chamber 2 to the exhaust system, whereby gases can be switched into the process chamber 1 only when required for processing. This also allows means for ensuring stable gas composition and flow to be maintained prior to switching into the process chamber.

The following equations indicate the steps of generating a ClF$_3$ gas.

$$Cl_2 + F_2 \rightarrow 2ClF \quad (1)$$

$$2ClF + 2F_2 \rightleftharpoons 2ClF_3 \quad (2)$$

Equation 1 shows the first step in the formation of ClF$_3$ from the reaction of Cl$_2$ and F$_2$. This occurs at temperatures in the range of 250 to 500° C. (preferably 350 to 400° C.) at atmospheric pressure. The second reaction step shown in equation 2 occurs at lower temperatures in the range of 200 to 350° C. (preferably 250 to 300° C.) at atmospheric pressure. Hence, the ClF$_3$ reactor system may comprise two different temperature controlled zones (or independent reactors), to control the individual reaction steps. Depending on the partial pressure of ClF$_3$ required a single reactor design may be sufficient, in this case operating at 250 to 350° C.

Details of the reactor design include:
1. premixing of the F$_2$ and Cl$_2$ using a static mixing technology, with low pressure drop throughout the reactor system (<50 Torr)
2. an HF trap located between the F$_2$ generator and the mixing stage
3. a high temperature reactor using static mixing technology (to improve heat transfer to enhance reaction kinetics and ensure effective mixing of the gases Cl$_2$+F$_2$+ClF$_x$)
4. minimising temperature hot spots and ensuring that controlled thermal gradients are used.

Figure 2:
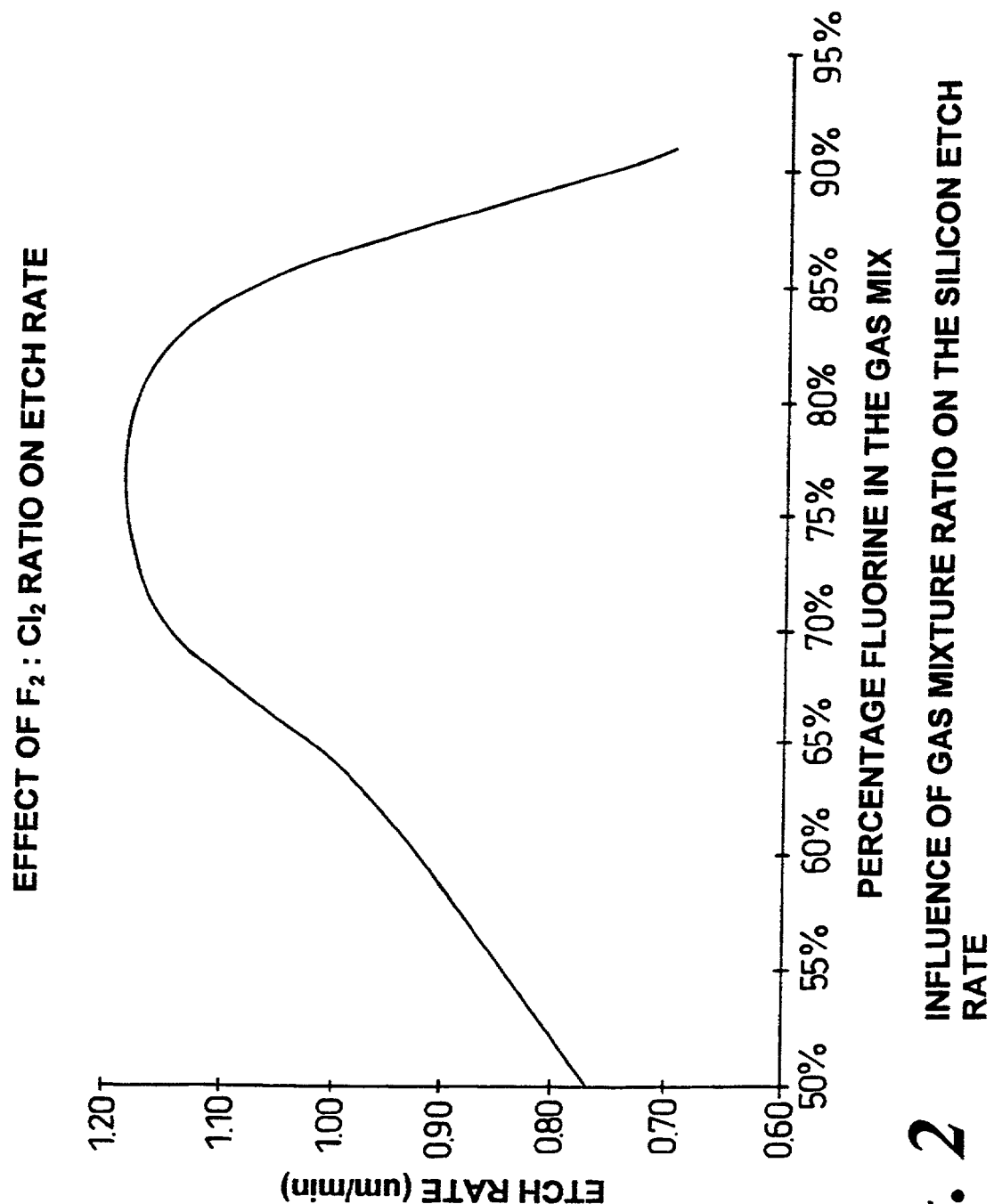
FIG. 2 illustrates the effect of gas ratio variations on silicon etch rate.

The use of ClF$_3$ necessitates a pre-conditioning of the gas lines and reactor/chamber surfaces to avoid any deleterious reactions, which may compromise safety (CJ Gugliemini and AD Johnson Semiconductor International, June 1999, pp 162–166). This preconditioning is necessary after every occasion where the surfaces have been exposed to the ambient atmosphere, which includes any maintenance operations. Ideally the pre-conditioning must be carried out using F$_2$. An additional feature of the present invention is the ability readily to perform the F$_2$ pre-conditioning. Practically this can be achieved for the whole system by flowing the F$_2$ only, with the reactor system between room and operational temperature, and operating the respective valving in order to pre-condition the necessary components of the system. If the pre-conditioning (and thermal cycling) of the reactor system is to be avoided, then a bypass valving arrangement can be used.

Where $ClF_3$ is required for plasma applications, it may be sufficient simply to combine the gases in a mixing manifold prior to entry into the plasma chamber without any specialised reaction chamber. As the plasma collisions serve to ionise the gas(es), so that the combination of radical and charged particle fluxes are used to carry out the processing, the function of $ClF_3$ may be equally well served by flowing appropriate ratios of $F_2:Cl_2$. FIG. 2 shows the result of etching silicon, comparing a $ClF_3$ plasma with a $F_2:Cl_2$ gas mixture. The result shows that the etch rate peaks at approximately 18–30% chlorine, which is in a similar range as the ratio of Cl:F as in $ClF_3$. Thus one embodiment of the present invention is the use of a $Cl_2/F_2$ gas mixture (preferably at 15 to 35% Cl, preferably 20–30% Cl) to replace the need for $ClF_3$.

One embodiment of the invention is the use of an additional $ClF_x$ holding chamber 11 (shown in FIG. 3) which serves to allow immediate gas flow on demand to reduce the processing time associated with generation startup or initialisation. The holding chamber is controlled to a temperature in the range 25 to 200° C. (preferably 25 to 100° C.) at atmospheric pressure.

Figure 3:
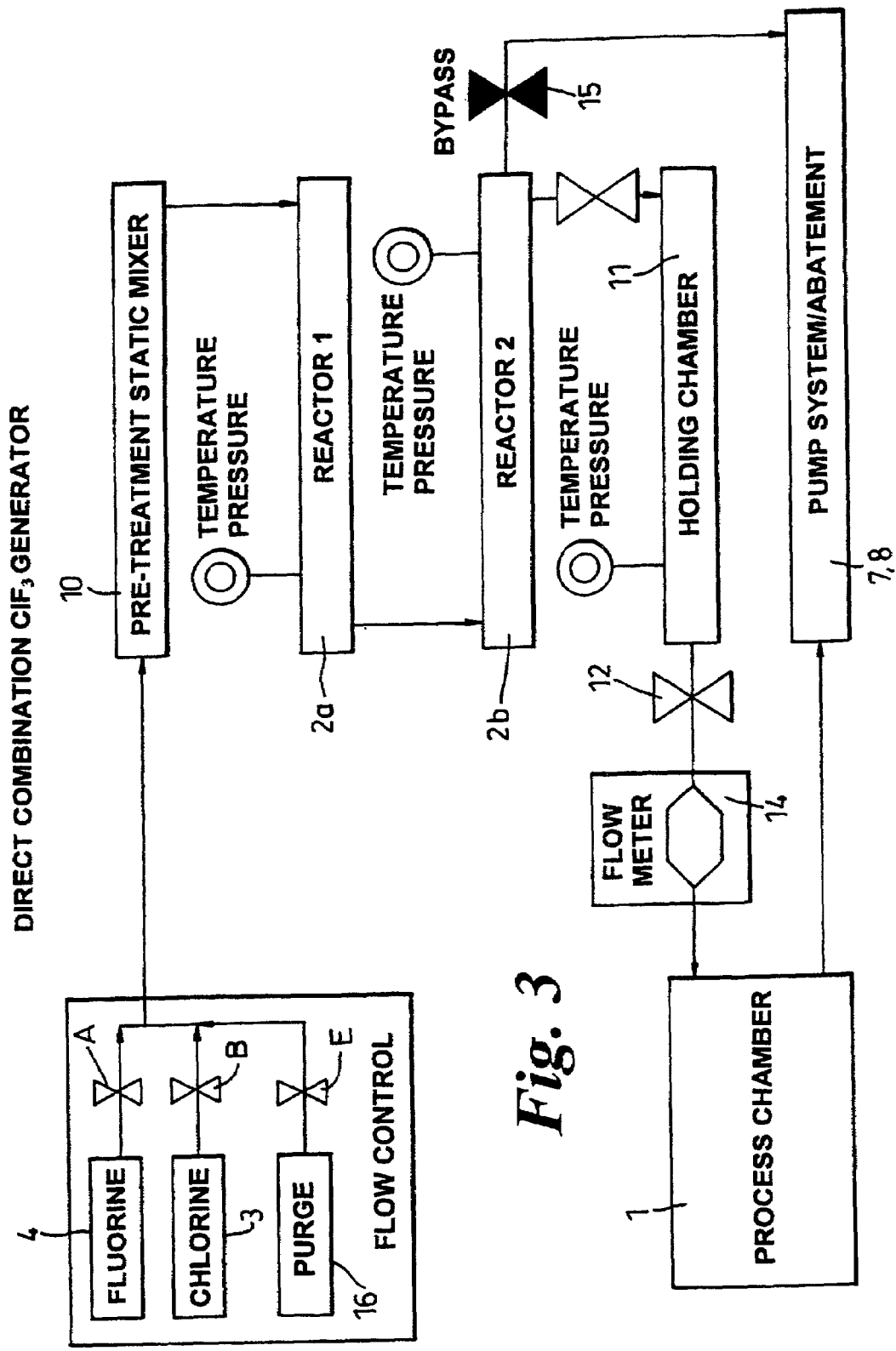
FIG. 3 is a diagrammatic illustration of a further example of a direct combination ClF$_3$ generator.

In FIG. 3, items similar to those in the embodiment 8 FIG. 3 are given similar reference numerals. In this embodiment $F_2$ and $Cl_2$ are supplied via respective control valves A and B to a pre-treatment static mixer 10. From the static mixer 10 the pre-mixed gases pass to a first reaction chamber 2a to allow reaction (1) above to take place and thence to a second reaction chamber 2b where reaction (2) takes place. The reaction mixture from the second reaction chamber 2b is then passed to a holding chamber 11, maintained at a required temperature and pressure, whence the reaction mixture passes via a valve 12 and flow meter 14 to the process chamber 1. The process chamber has an outlet connection to a pump system/abatement device 7,8. Also, the second reactor 2 may pass the reaction mixture direct to the pump system/abatement device 7,8 via a by-pass valve 15, to by-pass the holding chamber 11 and the process chamber 1. The flow bypass may be required for stabilisation purposes or, where the holding chamber is not present, for disposing of the reaction mixture during loading/unloading of the process chamber.

Also shown in the Figure is a source 16 of a purge gas for allowing purging of the system, under control of a valve E.

What is claimed is:

1. A method of generating $ClF_3$ gas using a $ClF_3$ gas generation system wherein supply sources of chlorine and fluorine are connected into a gas reaction chamber enabling generation of $ClF_3$ gas, and the reaction chamber has a valved outlet for the supply of the $ClF_3$ gas, wherein the precursor gases are fed from the supply sources to the reaction chamber, a combination reaction is performed and the $ClF_3$ reaction is fed on to a local processing chamber or tool.

2. A method according to claim 1 wherein the gasses formed are fed into a plasma chamber using $Cl_2/F_2$ gas mixture, wherein the chlorine level is between 15–35%.

3. A method according to claim 1 wherein an additional $ClF_x$ gas is provided in a holding chamber which allows immediate gas flow on demand to reduce processing time.

4. A method according to claim 1 wherein the gas lines and reactor surfaces are pre-conditioned using $F_2$.

5. A method according to claim 1 wherein the gasses formed are fed into a plasma chamber using $Cl_2/F_2$ gas mixture, wherein the chlorine level is between 20–30%.

* * * * *